(12) United States Patent
Gonzalez

(10) Patent No.: US 7,094,416 B2
(45) Date of Patent: Aug. 22, 2006

(54) FACIAL TREATMENT MASK AND THE PROCESS FOR ITS PREPARATION

(75) Inventor: Jose Sequi Gonzalez, Paterna (ES)

(73) Assignee: Emprediver, S. L., (ES)

( * ) Notice: Subject to any disclaimer, the term of this patent is extended or adjusted under 35 U.S.C. 154(b) by 0 days.

(21) Appl. No.: 11/184,252

(22) Filed: Jul. 19, 2005

(65) Prior Publication Data

US 2005/0249765 A1    Nov. 10, 2005

Related U.S. Application Data

(63) Continuation of application No. PCT/ES2003/000030, filed on Jan. 22, 2003.

(51) Int. Cl.
*A61K 8/02* (2006.01)
*A61K 31/74* (2006.01)
*A61K 33/08* (2006.01)
*A61K 33/06* (2006.01)
*A01N 65/00* (2006.01)

(52) U.S. Cl. .................. 424/401; 424/78.03; 424/692; 424/696; 424/757; 514/770

(58) Field of Classification Search ...................... None
See application file for complete search history.

(56) References Cited

FOREIGN PATENT DOCUMENTS

| EP | 0511451 A | 11/1992 |
| EP | 1186291 | 3/2002 |
| ES | 2010456 A | 11/1989 |

OTHER PUBLICATIONS

International Cosmetic Ingredient Dictionary, vol. 1, "Titanium Dioxide", 1993.*
International Search Report, Jun. 17, 2003 (3 pages).

* cited by examiner

*Primary Examiner*—Sreeni Padmanabhan
*Assistant Examiner*—Marina Lamm
(74) *Attorney, Agent, or Firm*—St. Onge Steward Johnston & Reens, LLC

(57) ABSTRACT

It discloses a facial treatment mask that can be applied directly on the user's skin, with improved organoleptic properties, along with a process for preparing the product that serves as a base for the mask. Said product consists of the mixture of two separate phases, immediately prior to application. Each phase consists of a series of ingredients which give them their appearance of a suspension and gel respectively, so that when combined together, they form a genuine emulsion. The process for preparing each phase includes various steps of mixing and combining their respective ingredients, with the help of blending and kneading devices that operate for pre-determined periods of time. The application is conducted within a maximum period of approximately 4 to 5 minutes, and the polymerisation or setting is achieved within a minimum time frame of approximately 15 minutes.

8 Claims, No Drawings

FACIAL TREATMENT MASK AND THE PROCESS FOR ITS PREPARATION

This application is a continuation of pending International Patent Application No. PCT/ES2003/000030 filed Jan. 22, 2003 which designates the United States.

FIELD OF THE INVENTION

The present invention relates to a facial treatment mask and to the process for its preparation, which incorporates essential innovative characteristics and provides notable advantages in comparison with the methods and devices known and used for the same purpose in the current state of the art.

More specifically, the invention proposes the preparation of a mask of the type known as "peel-off", especially suited for the specified purpose, with determined physicochemical and organoleptic properties, and with the special characteristic constituting a genuine emulsion as it incorporates two phases, as is typical of these types of compositions, namely a water phase and an oil phase, in such a way that once both phases are mixed together, they are capable of polymerisation. To apply the mask it is spread over the surface to be treated using a spatula, and the polymerisation reaction starts following an established period of time from the moment of application.

The field of application of the invention is obviously included in the industrial sector dedicated to the manufacture and sale of cosmetic and beauty products in general.

BACKGROUND AND SUMMARY OF THE INVENTION

Everyone in general is aware of the use of certain types of treatments and creams for cosmetically treating skin to maintain it in its best possible physical and aesthetic condition. In this respect, for a considerable amount of time, the application on skin, in particular of the face or of other parts of the body, of products that can form a mask is well-known which, after a certain amount of time remaining on the skin's surface, can be removed simply by peeling off with the hands.

The products that can be used for the specified purpose have evolved considerably in the course of the last few years. The current applicant has conducted a detailed ongoing investigation into this field, which has allowed it to overcome in time a series of successive stages, starting from an initial product stage that consisted of preparing a mixture involving a powder phase that was simply mixed with tap water, to an intermediate stage in which the masks in question consisted of a gel phase and a powder phase (according to four different models), up until today when it has been possible to create the mask of the invention, which is the object of the description that follows.

At present, there are other masks that comprise a water phase and a powder phase, which are capable of setting once they are combined, by virtue of the effect of polymerisation. There are also other mask preparations that comprise a gel phase and a powder phase, similar to the one mentioned above as an intermediate stage in the current applicant's products.

Unlike that existing in the current state of the art, the present invention has been developed in a direction that is clearly distinguished with respect to existing knowledge, because it allows a mask to be produced which is based on two separate phases, in such a way that, once they are blended together, the resulting combination constitutes a genuine emulsion, capable of setting by polymerisation. The mixture comprises a water phase and an oil phase. In this way, the mask of the invention provides the additional advantage of allowing active ingredients to be incorporated together with liposoluble and hydrosoluble compounds that can provide it with greater enrichment for treating the skin from the cosmetic point of view.

The invention also relates to the process for preparing each of the two phases that go into the mixture, to produce the product that can be applied as a mask on the user's skin.

DETAILED DESCRIPTION OF A PREFERRED EMBODIMENT

As already indicated above, the mask of the invention consists basically of a mixture that is produced from two phases that can be mixed together by the user immediately prior to its application. Consequently, both phases are presented to the user properly protected and enclosed in specially designed recipients, of which at least one will be used for the purpose of mixing the two phases together. According to a preferred embodiment of the invention, the ingredients that comprise each of the phases and their approximate percentages in weight respectively, are the ones set out below:

Phase 1

| Ingredient | Weight Percentage |
| --- | --- |
| Liquid paraffin | 39.21% |
| Calcium sulphate | 21.00% |
| Diatomaceous earth | 12.50% |
| Algin | 8.00% |
| Isoprene/styrene hydrogenated copolymer | 5.40% |
| Capric/caprylic triglyceride | 3.60% |
| Glycine soja | 3.00% |
| Magnesium oxide | 3.00% |
| CI 77891 | 3.00% |
| Sodium phosphate | 0.80% |
| Phenoxyethanol | 0.10% |
| Methylparaben | 0.06% |
| Propylparaben | 0.01% |
| Ethylparaben | 0.01% |
| Butylparaben | 0.01% |
| Perfume (sage oil) | 0.30% |

Phase 2

| Ingredient | Weight Percentage |
| --- | --- |
| Water | 93.46% |
| Algin | 5.70% |
| Imidazolidinyl urea | 0.50% |
| Sodium methylparaben | 0.12% |
| Mica | 0.05% |
| Titanium oxide | 0.05% |
| Methylchloroisothiazolinone | 11.5 ppm |
| Methylisothiazolinone | 3.5 ppm |
| Perfume (sage oil) | 0.02% |

Each of the phases constituted accordingly, present certain physicochemical characteristics, which are set out below:

Phase 1:

| Cosmetic presentation: | Suspension |
| --- | --- |
| Colour: | Intense white |
| Aroma: | Sage |
| Density (at 20° C.): | 1160–1170 g/l |
| Viscosity: | >500000 mPa:s |
| (Brookfield 65° C., sp = 11, 0.5 rpm) | |
| Mechanical stability: | 30 minutes/3000 rpm without separation |
| Thermal stability: | 24 h/45° C. Without separation |

Phase 2:

| Cosmetic presentation: | Gel |
| --- | --- |
| Colour: | Faded white |
| Aroma: | Sage |
| Appearance: | Pearly |
| Density (at 20° C.): | 1020–1025 g/l |
| pH: | 7.00–8.50 |
| Viscosity: | >40000 mPa:s |
| (Brookfield, 30° C., sp = 11, 10 rpm) | |
| Mechanical stability: | 30 min/3000 rpm without separation |
| Thermal stability: | 24 h/45° C. without separation |

According to the present example that is the object of this description, each phase is presented to the user in a separate form. The first of them (Phase 1) in a 20 g dose, in a (PS) polystyrene bowl with a 150 ml capacity, sealed with a heat-sealable sheet coated with aluminium and polythene; the other phase (Phase 2) for its part presented in a 105 g dose, inside a flexible (LDPE) low density polyethylene tube, with a 100 ml capacity.

When preparing the mask, the user must follow a series of successive steps, as indicated below:

remove the seal from the bowl containing the first phase;

empty the contents of the tube of the second phase into the bowl of the first phase;

using a spatula or other similar utensil, mix the two phases together thoroughly and vigorously for at least 45 seconds;

using the same spatula or other similar utensil, apply the mixture on the area to be treated, for a time that should preferably not exceed 4 minutes;

next, allow the mask to act for a period of at least 15 minutes, after which the mask can be removed, entirely set, in a single piece;

finally, after removing the mask, an oily film may be observed to remain on the skin, enabling a light massage to be applied.

The product prepared for the application as described above has well-defined organoleptic characteristics. Thus, after thoroughly mixing the two phases in the bowl of the first phase during said period of at least 45 seconds, the product that is produced consists of viscous gel of intense white colour that gives off a sage aroma, and is creamy in appearance. The characteristics of this gel make it easy to apply and spread over the surface to be treated, using a spatula or similar, as already mentioned, for a period of approximately 4 or 5 minutes. After this time, the polymerisation reaction begins which makes the product become gradually harder until when, after a period of approximately 15 minutes after producing the mixture, the polymerisation is complete. If the mask is removed after said 15-minute period, the mask will come off in a single piece, and the polymerised product will have a certain degree of elasticity, a large degree of flexibility, and will be resistant to breakage and pleasant to the touch.

Understandably, the mask applied from the product produced by combining the two phases described in the paragraphs above, has very noticeable advantages, both from the point of view of its preparation and application, and from the point of view of the achieved results.

The process for preparing each of the two phases consists of a series of successive steps, which have been perfectly defined and distinguished, and are described below given that they also form part of the present invention.

Thus, first of all, in respect of phase 1, the preparation takes place as follows:

1) First Stage: Grinding of the Texturised Soy

For this operation, 500 g of texturised soy are measured and put into a grinding machine, and the grinding operation takes place for a set amount of time and at a pre-established speed. In the example of embodiment of the present invention, an appliance of the type known as a "Thermomix" was used, and the grinding time was of about 1 minute with the revolutions device set to number 11.

2) Second Stage: Formation of a White Powder

In this second stage, a white powder is formed, with the following composition:

| TC 901 AF alginate | 70.50% |
| --- | --- |
| Calcium sulphate 2-hydrate, aditio quality | 22.00% |
| LC 981 Unipure White | 6.00% |
| Texturised soy, ground | 1.50% |

To prepare this white powder, first of all each of the ingredients that are listed in the above formula are measured in the established order, using a suitable recipient with sufficient capacity to contain the amount that needs to be prepared. This compound is emptied, either directly or using a small vessel into a V-shaped mixer and with both blades in operation, the mixing is maintained for a period of time, which is preferably in the region of 15 minutes.

3) Third Stage: Embodiment of the Phase 1 Product

To form this product, a suitable recipient is prepared to contain the amount of product that is to be made, and the following ingredients are weighed:

a) Transgel: common name for a compound that consists of liquid paraffin, styrene/isoprene hydrogenated copolymer and capric/caprylic triglyceride;

b) Phenonip: common name for a compound that includes ingredients such as phenoxyethanol, methylparaben, polyparaben, ethylparaben and butylparaben, and c) Sage oil.

Next, these compounds are placed in a kneading machine and the white powder is weighed in the same recipient, which is then also added to the kneading machine using spatulas to scrape off any remains of the product left on the recipient of weighed ingredients. The kneading machine is switched on and left to operate for a period of approximately 20 minutes.

Continuing with the manufacturing process, and in relation to the second phase required to produce the product from which the cosmetic mask will be produced, the process is as follows:

In a suitable recipient, with sufficient capacity to contain the amount of product to be prepared, half of the water is weighed along with the rest of the ingredients that are involved in the preparation of this phase (with the exception of the sage oil). The other half of the water is measured in a separate recipient, and put aside until it is required. The sage oil is measured in a test-tube and also put to one side until required;

Next, the first recipient, which is the one that will be used as the basis for manufacturing the product, is placed in a mixer of suitable characteristics. Once it has been placed, the mixer's gear wheel is set at its lowest position, after which the mixer is switched on, at an initial pre-established speed;

Once the mixer has been switched on, it will be observed that the mixture starts to thicken rapidly; at this point, the second half of the water that was set aside in the second recipient is added, and the mixing is maintained at the lowest point and at the same initial speed. After, the sage oil is added and gradually the rotating speed is increased up to a second pre-determined speed. This last speed is maintained until the manufacturing process is complete. The rotating blade is moved up and down gradually, with a view to breaking up any lumps that may have formed at the outset. Because the lumps rise to the surface of the gel that is formed, the mixing must be maintained, as well as the lifting and lowering actions until the formation of lumps is no longer detected. The minimum time considered appropriate is approximately 30 minutes.

According to the example of preferred embodiment, the first speed required for the mixer, is in the region of one thousand revolutions per minute, while said second speed is in the region of two thousand five hundred revolutions per minute.

Understandably, the two phases thus produced can now be packaged separately, to be presented to the user in the form described above.

At the same time, it must also be understood that the composition and preparation conditions described for both phases 1 and 2, in fact constitute only one of the possible embodiments and, consequently, may be subject to variation, with a view to adapting the ingredients to each particular case, or even to provide either of the two phases with certain specific properties.

What is claimed is:

1. Facial treatment mask designed for the cosmetic treatment of skin, of the type that can be applied to the area to be treated through being spread with a spatula or other similar utensil, and of the type that hardens or polymerises after a set period of time, characterised in that it consists of two different phases, dosed in separate recipients, and capable of being mixed together prior to application, with the first phase consisting of:

| | |
|---|---|
| Liquid paraffin | 39.21% |
| Calcium sulphate | 21.00% |
| Diatomaceous earth | 12.50% |
| Algin | 8.00% |
| Styrene/isoprene hydrogenated copolymer | 5.40% |
| Capric/caprylic trigliceride | 3.60% |
| Glycine soja | 3.00% |
| Magnesium oxide | 3.00% |
| CI 77891 | 3.00% |

-continued

| | |
|---|---|
| Sodium phosphate | 0.80% |
| Phenoxyethanol | 0.10% |
| Methylparaben | 0.06% |
| Propylparaben | 0.01% |
| Ethylparaben | 0.01% |
| Butylparaben | 0.01% |
| Perfume (sage oil) | 0.30% | and with the second phase consisting of:

| | |
|---|---|
| Water | 93.46% |
| Algin | 5.70% |
| Imidazolidinyl urea | 0.50% |
| Sodium methylparaben | 0.12% |
| Mica | 0.05% |
| Titanium oxide | 0.05% |
| Methylchloroisothiazolinone | 11.5 ppm |
| Methylisothiazolinone | 3.5 ppm |
| Perfume (sage oil) | 0.02%. |

2. Facial treatment mask according to claim 1, characterised in that said first phase is presented in the form of a suspension, of intense white colour, with a sage aroma, and a creamy appearance, with a density (measured at 20° C.) in the region of 1160 to 1170 g/l, a Brookfield viscosity of >500000, a mechanical stability of 30 min/3000 rpm without separation and thermal stability of 24 h/45° C. without separation.

3. Facial treatment mask according to claim 1, characterised in that said second phase is presented in the form of a gel, of faded white colour, with a sage aroma, and a pearly appearance, with a density (measured at 20° C.) in the region of 1020 to 1025 g/l, a pH of 7.00 to 8.50, with a Brookfield viscosity of >40000, a mechanical stability of 30 min/3000 rpm without separation and a thermal stability of 24 h/45° C. without separation.

4. Facial treatment mask according to claim 1, characterised in that the product that it consists of is produced by thoroughly and vigorously mixing the abovementioned phases 1 and 2, for a minimum time of 45 seconds.

5. A method for cosmetic facial treatment comprising (1) mixing the two phases of the facial treatment mask according to claim 1 and (2) applying to the user's skin the resulting facial treatment mask using a spatula or other similar utensil.

6. The method according to claim 5, characterized in that the application is achieved in a period that does not exceed 4 minutes.

7. The method according to claim 5, characterized in that the mask is allowed to remain on the skin for a period of at least 15 minutes.

8. The method according to claim 5, further comprising removing the mask from the skin, wherein the mask forms a single piece and leaves on the skin an oily film.

* * * * *